United States Patent [19]

Bollingen et al.

[11] 4,259,523

[45] Mar. 31, 1981

[54] ORGANIC COMPOUNDS

[75] Inventors: Pietro Bollingen, Bottmingen; Manfred Krieger, Pratteln, both of Switzerland

[73] Assignee: Sandoz Ltd., Basel, Switzerland

[21] Appl. No.: 37,719

[22] Filed: May 11, 1979

Related U.S. Application Data

[63] Continuation of Ser. No. 914,401, Jun. 12, 1978, abandoned, which is a continuation of Ser. No. 740,182, Nov. 9, 1976, abandoned, which is a continuation-in-part of Ser. No. 697,403, Jun. 18, 1976, abandoned.

[51] Int. Cl.³ .............................................. C07C 177/00
[52] U.S. Cl. ................................. 562/500; 542/429; 542/430; 546/67; 548/253; 548/342; 560/53; 560/60; 560/61; 560/118; 560/121; 562/470; 562/471; 562/463; 562/503; 424/305; 424/308; 424/317
[58] Field of Search ...................... 560/118; 562/500

[56] References Cited

FOREIGN PATENT DOCUMENTS 817383 1/1975 Belgium ................................. 560/118

Primary Examiner—Robert Gerstl
Attorney, Agent, or Firm—Gerald D. Sharkin; Robert S. Honor; Timothy G. Rothwell

[57] ABSTRACT

This invention provides new mono-deuterated prostaglandins having prolonged uterotonic activity.

3 Claims, No Drawings

ORGANIC COMPOUNDS

This is a continuation of application Ser. No. 914,401, filed June 12, 1978, which in turn is a continuation of application Ser. No. 740,182, filed Nov. 9, 1976, which in turn is a continuation-in-part of Ser. No. 697,403, filed June 18, 1976, all now abandoned.

The present invention relates to deuterated prostaglandins and intermediates for their production. It is to be appreciated that the present prostaglandings and intermediates are non-radioactive in the sense that they do not contain, e.g. hydrogen, atoms containing more than the natural amount of radioactive isotopes, e.g. tritium.

In particular, the present invention provides monodeuterated, 15-hydroxy group-containing prostaglandins, the deuterium atom being attached to the carbon atom in the 15-position. Such prostaglandins may be in racemic form or optically active form.

The present invention also provides a process for the production of such mono-deuterated, 15-hydroxy group-containing prostaglandins, which comprises splitting off the protecting group or groups in a corresponding prostaglandin having a deuterium atom attached to the carbon atom in the 15-position and in which at least one hydroxy and/or carboxylic acid group is protected.

In another aspect the present invention provides compounds of formula I,

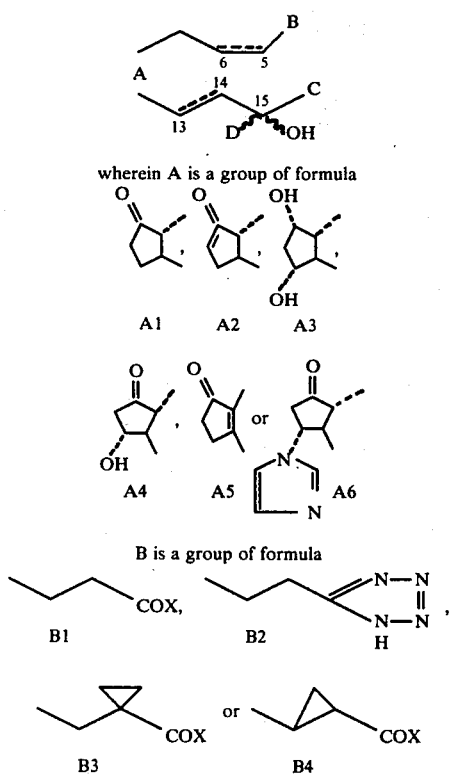

wherein
X is hydroxy, alkoxy of 1 to 10 carbon atoms, lysergyloxy, lysergylamino or dihydrolysergylamino, and
C is a prostaglandin end group.
A is preferably A2, A3 or A4.
B is preferably B1 or B4. X is preferably hydroxy or alkoxy. When X is alkoxy it is preferably of 1 to 4 carbon atoms, especially methoxy or ethoxy. In B4 it is to be appreciated that the substituents of the cyclopropyl ring are trans to each other.

C is a prostaglandin end group which corresponds to that of a natural or synthetic prostaglandin. In particular C may be a hydrocarbyl group conveniently containing up to 16 carbon atoms which may contain a cyclic moiety and/or may contain unsaturation and/or may contain a heteroatom, such as oxygen. Prostaglandin end groups which are contemplated include
(a) alkyl of 1 to 16 atoms, particularly a group

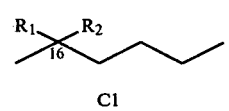

wherein $R_1$ and $R_2$ are independently hydrogen or alkyl of 1 to 4 carbon atoms,
(b) a group

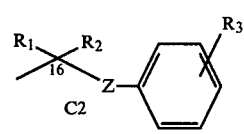

wherein
$R_1$ and $R_2$ are as defined above,
Z is —$CH_2$— or —O—,
$R_3$ is hydrogen, fluorine, chlorine or trifluoromethyl,
(c) alkenyl of 3 to 10 carbon atoms, or
(d) cycloalkyl of 3 to 10 carbon atoms which is unsubstituted or substituted by alkyl of up to 6 carbon atoms.

C is preferably C (a) as defined above. $R_1$ and/or $R_2$ when alkyl are preferably of 1 or 2 carbon atoms, especially methyl. When one of $R_1$ and $R_2$ is alkyl and the other of $R_1$ and $R_2$ is hydrogen, the 16 carbon atom may have the R or S configuration.

It will be appreciated that D stands for deuterium.

As indicated by the wavy lines in formula I the hydroxy group attached to the 15-carbon atom may have the α- or β-configuration.

As indicated by the broken lines in formula I, the 5 and 6 carbon atoms may be linked by a single bond or a cis double bond, and the 13 and 14 carbon atoms may be linked by a single bond or a trans double bond.

The present invention further provides a process for the production of a compound of formula I as defined above, by splitting off with acid an acid sensitive protecting group or groups present in a compound of formula II,

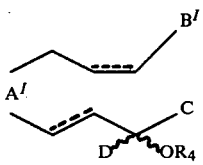

wherein $A^I$ is A as defined above, or

-continued

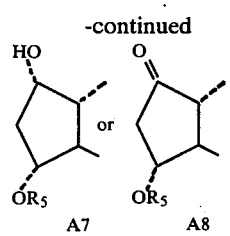

wherein
R$_4$ and R$_5$ are, independently, hydrogen or an acid sensitive protecting group,
B$^I$ is B as defined above, or

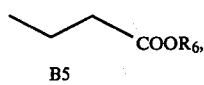

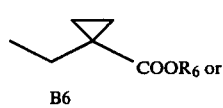

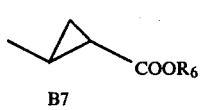

wherein
R$_6$ is an acid sensitive protecting group, and
C is as defined above,
with the proviso that there is present at least one acid sensitive protecting group.

The deprotecting process as defined above may be effected in conventional manner for such reactions.

Preferably the protecting group is a group stable to basic conditions. Suitable groups include tetrahydropyranyl and tert.-butyldimethylsilyl. Suitable conditions are well known in the art, e.g. acetic acid/tetrahydro-furan/water; methanol/hydrochloric acid; sulphuric acid; acetone/hydrochloric acid. Suitable temperatures are from −10° to 50° C., preferably room temperature.

It will be appreciated that the prostaglandins of formulae I and II may be interconverted into other prostaglandins of formulae I and II respectively, e.g. in conventional manner for such reactions.

For example, lysergyl esters, lysergyl amides and dihydro-lysergylamides may be made in conventional manner for producing such esters and amides, e.g. as in Example 32. Additionally, the moiety A2 may be changed into a moiety A6 by reaction with imidazole in conventional manner for the addition of an amine to the double bond of an α,β unsaturated ketone. Suitable conditions include reacting with imidazole at room temperature over several days. The imidazole may be in free form or the form of carbonyldiimidazole. Further reaction conditions are apparent from Example 33 which it is appreciated involves both ester formation and conversion from moiety A2 into A6.

The compounds of formula II may also be prepared in conventional manner. For example a compound of formula III,

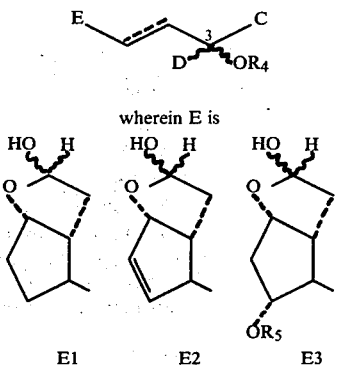

wherein E is and R$_4$, R$_5$ and C are as defined above, may be reacted under Wittig conditions with a compound of formula IV, $$(C_6H_5)_3P^\oplus\text{—}CH^\ominus\text{—}B \qquad IV$$

wherein B is as defined above, with, if desired, further reaction of the resulting product according to methods known in the prostaglandin art, e.g. selective oxidation at the 9 position.

A compound of formula III, as defined above, may be produced by selectively reducing the lactone moiety in a compound of formula V,

wherein
C is as defined above,

F is

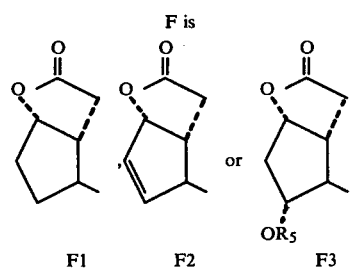

R$_4$ and R$_5$ are as defined above, in conventional manner, e.g. using diisobutylaluminium hydride.

The invention further provides a process for the production of a compound of formula V, which comprises deuterating a compound of formula VI,

wherein
C is as defined above, and
F$^I$ is F1, F2, F3 or

F4 wherein R7 is hydrogen or a bulky group capable of influencing the proportion of α:β alcohol formed, and if necessary converting any group R7 present into a group R5 as defined above, and if desired protecting the 3-hydroxy group with an acid sensitive protecting group.

The reaction may be carried out in conventional manner for such deuterations bearing in mind the other groups present. For example a deuterating agent such as sodium or zinc borodeuteride may be used. An anhydrous inert organic solvent such as dimethyl formamide or dimethoxyethane may be present. Suitable temperatures are between −40° and 50° C. Preferably the reaction is effected under an inert gas atmosphere.

The α- and β-alcohols which may both be formed may be separated in conventional manner.

The group R7 may be chosen such that it influences by virtue of its size the proportion of α:β alcohol formed generally increasing the amount of α-alcohol. Such groups are well known in the art.

An example of a suitable protecting group R7 is paraphenylbenzoyl or benzoyl. Such groups are split off under alkaline conditions, and may be exchanged for a group R5 in conventional manner.

The 3-hydroxy group may be protected in conventional manner.

Free forms of prostaglandins being suitably basic, e.g. a compound of formula I, wherein A is A6, or X is lysergyloxy, lysergylamino or dihydrolysergylamino, may be converted into acid addition salts forms in conventional manner and vice versa. A suitable acid is methanesulphonic acid. Free forms of prostaglandins being suitably acidic, e.g. a compound of formula I, wherein X is hydroxy, may be converted into cationic salt forms in conventional manner and vice versa. A suitable cation is the sodium cation.

Insofar as the production of any starting material is not particularly described these compounds are known, or may be produced and purified in accordance with known processes, or in a manner analogous to processes described herein, e.g. in the Examples, or to known processes.

It will be appreciated that optically active products may be obtained from optically active starting materials.

The deuterated prostaglandins of the invention, especially the compounds of formula I exhibit interesting pharmacological activity. In particular the deuterated prostaglandins exhibit the same type of activity as the non-deuterated analogues, but have a longer duration of action. Thus the cmpounds of formula I in general, and especially the PGE and PGF$_\alpha$ compounds exhibit uterotonic activity, as indicated by a uterotonic effect on the rat uterus in situ according to the principles of Bisset G. W. et al., Memoirs of the Society for Endocrinology No. 14-Endogenous substances affecting the myometrium. Edited by W. R. Pickles and R. J. Fitzpatrick, Cambridge University frey 1966, p. 185–198.

The deuterated prostaglandins may be administered in the same way and at the same dosage as the non-deuterated analogues. If the prostaglandin is suitably basic a pharmacologically acceptable acid addition salt form may be used. If the prostaglandin is suitably acidic a pharmacologically acceptable cationic salt form may be used. Such salt forms are readily made in conventional manner from the free form and exhibit the same order of activity as the free form. Accordingly the present invention also provides a pharmaceutical composition comprising a mono-deuterated 15-hydroxy group-containing prostaglandin, the deuterium atom being attached to the carbon atom in the 15 position, or a compound of formula I, in association with a pharmaceutical carrier or diluent. Such compositions may be formulated in conventional manner so as to be, for example, a solution or tablet.

A group of compounds of formulae I and V comprises those wherein C is Cl wherein R1 and R2 are independently hydrogen or methyl, or C2 wherein Z is O and R3 is p- or m-fluoro- or p- or m-chloro or m-trifluoromethyl.

In the following Examples all temperatures are in degrees Centigrade and are uncorrected.

I.R. refers to characteristic bands exhibited in the infra-red spectrum of a methylene chloride solution.

EXAMPLE 1

15-Deutero-11α,15R-dihydroxy-16,16-dimethyl-9-keto-2,3-(−)-trans-methylene-prosta-5cis, 13trans-dienoic acid 400 mg of 15-deutero-11α,15α-bis-tetrahydropyranyloxy-16,16-dimethyl-9-keto-2,3-(−)-trans-methylene-prosta-5cis,13trans-dienoic acid tert.-butyldimethyl silyl ester is dissolved in 18 ml of a mixture of equal parts by volume of acetic acid, tetrahydrofuran, and water. The reaction mixture is maintained for 38 hours at room temperature, and then evaporated under a vacuum. The residue is chromatographed on silica gel using chloroform+2% methanol as eluant to yield the pure title compound.

IR: 3550, 3400, 1720, 1696 cm$^{-1}$.

In analogous manner to that described in Example 1 the following compounds of formula I are obtained from the corresponding 15-tetrahydropyranyl ether. When there is an 11-hydroxy group present in the final product the starting material is the appropriate 11,15-bis-tetra-hydropyranyl ether. When there is a 9-keto group and a carbonyl group present in the final product the carboxyl group is protected as the tert.-butyldimethyl silyl ester in the starting material; otherwise the free acid is used as the starting material for the production of a final compound having a carboxyl group.

EXAMPLE 2

15-Deutero-16,16-dimethyl-2,3-(+)-trans-methylene-9α,11α,15R-trihydroxy-prosta-5cis,13trans-dienoic acid.

IR: 3600, 3400, 1695 cm$^{-1}$.

EXAMPLE 3

15-Deutero-11α,15R-dihydroxy-16,16-dimethyl-9-keto-2,3-(+)-trans-methylene-prosta-5cis,13trans-dienoic acid.

IR: 3600, 3450, 1740, 1695 cm$^{-1}$.

EXAMPLE 4

15-Deutero-16,16-dimethyl-15R-hydroxy-2,3-(+)-trans-methylene-9-keto-prosta-5cis,10,13trans-trienoic acid.
IR: 3600, 1700, 1140 cm$^{-1}$.

EXAMPLE 5

15-Deutero-16,16-dimethyl-2,3-(+)-trans-methylene-9α,11α,15R-trihydroxy-prosta-5cis,13trans-dienoic acid methyl ester.
IR: 3600, 3400, 1720, 1710 cm$^{-1}$.

EXAMPLE 6

15-Deutero-16,16-dimethyl-2,3-(−)-trans-methylene-9α,11α,15R-trihydroxy-prosta-5cis,13trans-dienoic acid.
IR: 3600, 3500, 1715, 1700 cm$^{-1}$.

EXAMPLE 7

15-Deutero-16,16-dimethyl-2,3-(−)-trans-methylene-9α,11α,15R-trihydroxy-prosta-13-trans-enoic acid.
IR: 3550–3400, 1700 cm$^{-1}$.

EXAMPLE 8

15-Deutero-11α,15R-dihydroxy-16,16-dimethyl-9-keto-2,3-(−)-trans-methylene-prosta-13-trans-enoic acid.
IR: 3600–3400, 1740, 1695 cm$^{-1}$.

EXAMPLE 9

15-Deutero-16,16-dimethyl-15R-hydroxy-9-keto-2,3-(−)-trans-methylene-prosta-10,13trans-dienoic acid.
IR: 3600, 1700 cm$^{-1}$.

EXAMPLE 10

15-Deutero-2-ethylene-16,16-dimethyl-9α,11α,15R-trihydroxy-prosta-5cis,13trans-dienoic acid.
IR: 3400, 1690 cm$^{-1}$.

EXAMPLE 11

15-Deutero-2-ethylene-16,16-dimethyl-11α,15R-dihydroxy-9-keto-prosta-5cis,13trans-dienoic acid.
IR: 3400, 1740–1730, 1700–1680 cm$^{-1}$.

EXAMPLE 12

15-Deutero-2-ethylene-16,16-dimethyl-15R-hydroxy-9-keto-prosta-5cis,10,13trans-trienoic acid.
IR: 3600, 1710–1685 cm$^{-1}$.

EXAMPLE 13

16-n-butyl-15-deutero-2,3-(−)-trans-methylene-9α,11α,15S-trihydroxy-prosta-5cis,13trans-dienoic acid.
IR: 3550–3350, 1715–1680 cm$^{-1}$.

EXAMPLE 14

16-n-butyl-15-deutero-11α,15S-dihydroxy-9-keto-2,3-(−)-trans-methylene-prosta-5cis,13trans-dienoic acid.
IR: 3550–3350, 1745–1690 cm$^{-1}$.

EXAMPLE 15

16-n-butyl-15-deutero-15S-hydroxy-9-keto-(2,3)-(−)-trans-methylene-prosta-5cis,10,13trans-trienoic acid.
IR: 3600, 1745–1690 cm$^{-1}$.

EXAMPLE 16

15-Deutero-11α,15R-dihydroxy-9-keto-16R-methyl-2,3-(−)-trans-methylene-prostanoic acid.
IR: 3600–3300, 1740–1690 cm$^{-1}$.

EXAMPLE 17

15-Deutero-11α,15R-dihydroxy-9-keto-16R-methyl-2,3-(−)-trans-methylene-prosta-5cis-enoic acid.
IR: 3600–3350, 1735–1685 cm$^{-1}$.

EXAMPLE 18

15-Deutero-11α,15R-dihydroxy-16,16-dimethyl-9-keto-2,3-(−)-trans-methylene-prosta-5cis,13trans-dienoic acid methyl ester.
IR: 3600–3400, 1750–1700 cm$^{-1}$.

EXAMPLE 19

15-Deutero-16,16-dimethyl-9α,11α,15R-trihydroxy-17,18,19,20-tetranor-16-(3′-trifluoromethylphenoxy)-2,3-(−)-trans-methylene-prosta-5cis,13trans-dienoic acid.
IR: 3500–3300, 1730–1670 cm$^{-1}$.

EXAMPLE 20

1-Descarboxy-15-deutero-16,16-dimethyl-2-(5′-tetrazolyl)-9α,11α,15R-trihydroxy-17,18,19,20-tetranor-16-(3′-trifluoromethylphenoxy)-prosta-5cis,13trans-dienoic acid.
IR: 3500–3300 cm$^{-1}$.

EXAMPLE 21

15-Deutero-11α,15R-dihydroxy-16,16-dimethyl-2,3-(−)-trans-methylene-9-keto-17,18,19,20-tetranor-16-(3′-trifluoromethylphenoxy)-prosta-5cis,13trans-dienoic acid.
IR: 3500–3300, 1760–1720, 1720–1670 cm$^{-1}$.

EXAMPLE 22

15-Deutero-9α,11α,15S-trihydroxy-prosta-5cis,13-trans-dienoic acid lysergyl ester.
IR: 3550–3400, 1740 (broad).

EXAMPLE 23

15-Deutero-15S-hydroxy-11α-imidazol-1′-yl-9-keto-prosta-5cis,13trans-dienoic acid (1′-decanyl) ester.
IR: 3550–3350, 1740, 1720 cm$^{-1}$.

EXAMPLE 24

15-Deutero-15S-hydroxy-11α-imidazol-1′-yl-9-keto-prosta-13-trans-enoic acid lysergyl ester.
IR: 3500–3400, 1745, 1725, 1505 cm$^{-1}$.

EXAMPLE 25

15-Deutero-11α,15S-dihydroxy-9-keto-prosta-13trans-enoic acid lysergyl amide.
IR: (CH$_2$Cl$_2$+1% CH$_3$OH); 3400 (broad), 1745, 1665, 1525 cm$^{-1}$.

EXAMPLE 26

15-Deutero-16,16-dimethyl-9α,11α,15R-trihydroxy-prosta-5cis,13trans-dienoic acid.
IR: 3650–3300, 1750–1700 cm$^{-1}$.

EXAMPLE 27

15-Deutero-11α,15R-dihydroxy-16,16-dimethyl-9-keto-prosta-5cis,13-trans-dienoic acid.
IR: 3600–3300, 1760–1710, 1710–1690 cm$^{-1}$.

EXAMPLE 28

(±)-15-Deutero-15α-hydroxy-9-ketoprostanoic acid.
IR: 3550, 1760–1700 cm$^{-1}$.

EXAMPLE 29

(±)-15-Deutero-17,18,19,20-tetranor-16-[3'-trifluoromethylphenoxy]-9α,11α,15α-hydroxy-prosta-5cis,13trans-dienoic acid.
IR: 3600, 3350, 1710 cm$^{-1}$.

EXAMPLE 30

15-Deutero-11α,15R-dihydroxy-9-keto-16R-methyl-prosta-5cis-enoic acid methyl ester.
IR: 3700–3300, 1740 cm$^{-1}$.

EXAMPLE 31

15-Deutero-11α,15S-dihydroxy-9-keto-prosta-5cis,13trans-dienoic acid lysergyl ester.
IR: 1740 (broad) cm$^{-1}$.

Preparation of starting materials, e.g. for Example 1.

(a) (−)-2β-(3'-deutero-3'α-hydroxy-4',4'-dimethyl-trans-1'-octenyl)-5α-hydroxy-3α-para-phenylbenzoyloxy-1α-cyclo-pantyl acetic acid γ-lactone and
(−)-2β-(3'-deutero-3'β-hydroxy-4',4'-dimethyl-trans-1'-octenyl)-5α-hydroxy-3α-para-phenylbenzoyloxy-1α-cyclo-pentyl acetic acid γ-lactone (intermediate compounds of formula V having a bulky group R$_7$).

A solution of 1.45 g of (−)-5α-hydroxy-2β-(3'-oxo-4',4'-dimethyl-trans-1'-octenyl)-3α-para-phenylbenzoyloxy-1α-cyclopentyl acetic acid γ-lactone in 8 ml of absolute dimethoxyethane is added dropwise to a suspension of 2.26 g of zinc borodeuteride in 20 ml of absolute dimethoxyethane at −15° C. in a nitrogen atmosphere. Stirring is subsequently effected at 3° to 5° C. for 3.5 hours and at 5° to 10° C. for one hour. The mixture is then again cooled to −15° C. and 3 ml of an aqueous 10% (w/v) sodium hydrogen tartrate solution are slowly added. The mixture is extracted with 2×100 ml of ether. The organic phase is washed with 100 ml of a saturated aqueous sodium chloride solution, dried with sodium sulphate and concentrated by evaporation at reduced pressure, whereby a mixture of the corresponding α and β isomers is obtained. The residue is chromatographed on 50 g of neutral silicagel, whereupon the α- and then the β-isomer is eluted with chloroform (5% ethyl acetate).

α-isomer:
Thin layer chromatography (Silica gel): Methylene chloride (5% acetic ester) Rf=0.4, M.Pt. 107°–108° C.
IR (methylene chloride) inter alia bands at: 3500, 1770, 1710, 1660 cm$^{-1}$.

β-isomer:
Thin layer chromatography (Silica gel): Methylene chloride (5% acetic ester) Rf=0.3.
Spectral data approximately as for α-isomer.

The above mentioned (−)α isomer is reacted further in step (b) through to step (f) yielding optically pure product as follows:

(b) 2β-(3'-deutero-3'α-hydroxy-4',4'-dimethyl-trans-1'-octenyl)-3α,5α-dihydroxy-1α-cyclopentyl acetic acid γ-lactone (compound of formula V, wherein R$_5$=H).

A solution of 104 mg of sodium in 5.2 ml of absolute methanol is added at room temperature to a solution of 2.5 g of 2β-(3'-deutero-3'α-hydroxy-4',4'-dimethyl-trans-1'-octenyl)-5α-hydroxy-3α-para-phenyl-benzoyloxy-1α-cyclopentyl acetic acid γ-lactone in 104 ml of absolute methanol at room temperature. After 5 hours, the mixture is cooled to 10° C. and 6.3 ml of tartaric acid solution in methanol are added. The mixture is subsequently concentrated by evaporation at reduced pressure and the residue is taken up in 250 ml of methylene chloride. The organic phase is washed with 100 ml of saturated aqueous sodium chloride solution, is dried with sodium sulphate and concentrated by evaporation at reduced pressure. The residue is chromatographed on 150 g of silicagel. The compound is eluted with benzene (20% acetone). M.Pt. 82°–84° C.

(c) 2β-(3'-deutero-3'α-hydroxy-4',4'-dimethyl-trans-1'-octenyl)-3α,5α-dihydroxy-1α-cyclopentyl acetic acid γ-lactone-3,3'-bistetrahydropyranyl ether.

(Compound of formula V with acid sensitive protecting groups).

A solution of 1.6 g of 2β-(3'-deutero-3'α-hydroxy-4',4'-dimethyl-trans-1'-octenyl)-3α,5α-dihydroxy-1α-cyclopentyl acetic acid γ-lactone, 31 mg of p-toluenesulphonic acid monohydrate and 1.33 g of 3,4-dihydro-2H-pyrane in 103 ml of absolute toluene is produced at −10° C. and is then allowed to warm to room temperature. After one hour, the solution is washed with 50 ml of 10% (w/v) aqueous potassium bicarbonate solution and twice with 100 ml of saturated aqueous sodium chloride solution. The organic phase is dried with sodium sulphate and concentrated by evaporation at reduced pressure. The slightly yellow oily residue is chromatographed from 120 g of silicagel with toluene (+5% acetone), whereupon the pure title compound is isolated.

Thin layer chromatography (toluene; acetone; 2:1) Rf=0.7 (Silica gel).
IR: (methylene chloride) inter alia bands at 1770 cm$^{-1}$.

(d) 2β-(3'-deutero-3'α-hydroxy-4',4'-dimethyl-trans-1'-octenyl)-3α,5α-dihydroxy-1α-cyclopentyl-acetaldehyde-γ-lactol-3,3'-bis-tetrahydropyranyl ether (Compound of formula III)

8.73 ml of diisobutylaluminium hydride are slowly added dropwise to a stirred solution of 2.43 g of 2β-(3'-deutero-3'α-hydroxy-4',4'-dimethyl-trans-1'-octenyl)-3α,5α-dihydroxy-1α-cyclopentyl acetic acid γ-lactone-3,3'-bis-tetrahydropyranyl ether in 102 ml of absolute toluene cooled to −70° C. in a nitrogen atmosphere. The mixture is further stirred at −70° C. for one hour, and subsequently 65.3 ml of tetrahydrofuran:water (2:1) are carefully added over 30 minutes. The organic phase is washed with 150 ml of saturated aqueous sodium solution at room temperature, is dried with sodium sulphate and is concentrated by evaporation at reduced pressure. The resulting title compound is obtained as viscous oil.

IR: (methylene chloride) inter alia bands at: 3600, 1200 cm$^{-1}$.

(e) 15-deutero-16,16-dimethyl-9α-hydroxy-11α,15α-bis-tetra-hydropyranyloxy-2,3-(−)-trans-methylene-prosta-5cis,13trans-dienoic acid (compound of formula II, A=A7).

380 mg of sodium hydride are suspended in 3.8 ml of absolute dimethyl sulphoxide and are kept under nitrogen for 55 minutes at 75° C. Upon cooling, 2.1 ml of this solution are slowly added dropwise to a prepared solution of 1.89 g of triphenylphosphonium salt of 2-(2'-bromoethyl)-(−)-trans-cyclopropyl-1-carboxylic acid in 5 ml of absolute dimethyl sulphoxide and are stirred under nitrogen for 45 minutes to produce an ylide solution. 4 ml of the ylide solution are added at 20° C. to a prepared solution of 980 mg of 2β-(3'-deutero-3'α-hydroxy-4',4'-dimethyl-trans-1'-octenyl)-3α,5α-dihydroxy-1α-cyclopentyl-acetaldehyde-γ-lactol-3,3'-bis-tetrahydropyranyl ether in 3 ml of absolute dimethyl sulphoxide and 3 ml of absolute tetrahydrofuran. The reaction mixture is kept for 30 minutes at 55° C. Upon the addition of another 4 ml of ylide solution, stirring is effected for another 1.5 hours at 55° C. The cooled reaction mixture is poured into 100 g of ice, the aqueous phase is adjusted to pH 3–4, and is extracted thrice with chloroform. The organic phase is washed, dried and concentrated by evaporation at reduced pressure. The resulting crude product is chromatographed on 100 g of silicagel with chloroform with 1–5% methanol, whereupon the desired compound is obtained.

IR (methylene chloride) inter alia bands at: 3600, 3500, 1695 cm$^{-1}$.

(f) 15-deutero-16,16-dimethyl-9-keto-11α,15α-bis-tetra-hydropyranyloxy-2,3-(−)-trans-methylene-prosta-5cis,13trans-dienoic acid tert.-butyldimethyl silyl ester.

To 460 mg of 15-deutero-16,16-dimethyl-9α-hydroxy-11α,15α-bis-tetrahydropyranyloxy-2,3-(−)-trans-methylene-prosta-5cis,13trans-dienoic acid in 4.5 ml of absolute toluene, 137 mg of tert.-butyldimethyl chlorosilane are added under nitrogen to form the corresponding silyl ester. The reaction solution is cooled to 0° and 93 mg of triethylamine in 9 ml of absolute toluene are added. After stirring at 4 hours at room temperature, the reaction mixture is cooled to −25° C. and is slowly added dropwise to a solution of 500 mg of N-chloro-succinimide in 19 ml of absolute toluene and 0.33 ml of dimethylsulphide during the course of the next 30 minutes. After a further 3 hours 1 ml of triethylamine in 5 ml of pentane are added dropwise. The mixture is stirred for 25 minutes at room temperature and worked up with ether/water to give the desired starting material.

In analogous manner to that described above, prostaglandins are obtained from the following compounds of formula V, wherein R$_4$ and R$_5$ are both hydrogen derived from the corresponding 3-para-phenylbenzoyl and 3-benzoyl derivatives which are then converted into their corresponding 3,3'-bis-tetrahydropyranyl ethers.

(ba)* 2β-(3'-deutero-3'β-hydroxy-4',4'-dimethyl-trans-1'-octenyl)-3α,5α-dihydroxy-1α-cyclopentyl acetic acid γ-lactone.

(bb)* 2β-(3'-deutero-3'α-hydroxy-trans-1'-octenyl)-3α,5α-dihydroxy-1α-cyclopentyl acetic acid γ lactone.

(bc)* 2β-(3'-deutero-3'β-hydroxy-trans-1'-octenyl9-3α,5α-dihydroxy-1α-cyclopentyl acetic acid γ lactone.

(bd)* 2β-(3'-deutero-3'α-hydroxy-4'-methyl-trans-1'-octenyl)-3α,5α-dihydroxy-1α-cyclopentyl acetic acid γ-lactone.

(be)* 2β-(3'-deutero-3'β-hydroxy-4'-methyl-trans-1'-octenyl)-3α,5α-dihydroxy-1α-cyclopentyl acetic acid γ-lactone.

(bf)* 2β-(3'-deutero-4,4-dimethyl-3'α-hydroxy-trans-1'-octenyl)-5α-hydroxy-1α-cyclopent-3-enyl acetic acid γ-lactone.

(bg) 2β-(4-n-butyl-3'-deutero-3'S-hydroxy-trans-1'-octenyl)-3α,5α-dihydroxy-1α-cyclopentyl acetic acid γ-lactone.

(bh) 2β-(4-n-butyl-3'-deutero-3'S-hydroxy-trans-1'-octenyl)-5α-hydroxy-1α-cyclopent-3-enyl acetic acid γ-lactone.

(bi) 2β-(3'-deutero-3'R-hydroxy-4R-methyl-trans-1'-octenyl)-3α,5α-dihydroxy-1α-cyclopentyl acetic acid γ-lactone.

(bj) 2β-3'-deutero-3'R-hydroxy-4'-methyl-4'-[3"-trifluoromethylphenoxy]-trans-1-pentenyl9-3α,5α-dihydroxy-1α-cyclopentyl acetic acid γ-lactone.

(bk) 2β-(3'-deutero-3'S-hydroxy-trans-1'-octenyl)-3α,5α-dihydroxy-1α-cyclopentyl acetic acid γ-lactone.

(bl) 2β-(3'-deutero-3'S-hydroxhy-trans-1'-octenyl)-5α-hydroxy-1α-cyclopent-3-enyl acetic acid γ-lactone.

(bm)* 2β-(3'-deutero-3'α-hydroxy-octyl)-5α-hydroxy-1α-cyclo-pentyl acetic acid γ-lactone.

(bn)* 2β-(3'-deutero-3'α-hydroxy-4'-[3"-trifluoromethyl-phenoxy]-trans-1-butenyl)-3α,5α-dihydroxy-1α-cyclo-pentyl acetic acid γ-lactone.

*obtained in (±) racemic form and in 3'R or 3'S optically active form. Compounds (bd) and (be) may be obtained as the 4'α-methyl isomer of the 4'β-methyl isomer.

EXAMPLE 32

15-Deutero-9α-hydroxy-11α,15S-bis-tetrahydropyranyloxy-prosta-5cis,13 trans-dienoic acid lysergyl ester

[starting material for Example 22]

(a) ca. 275 mg of 15-deutero-9α-hydroxy-11α,15S-bis-tetra-hydropyranyloxyprosta-5cis,13 trans-dienoic acid is reacted with 167 mg of 2,2-dithiopyridine and 199 mg of triphenylphosphine in 5 ml of xylene at 20° for 24 hours. After evaporation of the solvent, the residual oil is chromatographed on Sephadex LH20 using methylene chloride+2% methanol to afford the corresponding 2-thiopyridyl ester.

(b) 190 mg of 15-deutero-9α-hydroxy-11α,15S-bis-tetrahydropyranyloxyprosta-5cis,13 trans-dienoic acid 2-thiopyridyl ester are reacted with 90 mg of lysergol in 5 ml of tetrahydrofuran at 20° C. for 24 hours. The reaction mixture is worked up on Sephadex LH20 with methylene chloride+0.5% methanol to obtain the title compound.

The starting materials for Examples 25 and 31 may be obtained in analogous manner using the appropriate starting materials.

EXAMPLE 33

15-Deutero-15S-tetrahydropyranyloxy-11α-imidazo-1'-yl-9-keto-prosta-13 trans-enoic acid lysergyl ester

[starting material for Example 24]

A solution of 180 mg of 15-deutero-15S-tetrahydropyranyloxy-9-keto-prosta-10,13 trans-dienoic acid in 4 ml of absolute dimethyl formamide may be reacted with 76 mg of carbonyldiimidazole and stirred under nitrogen for 3.5 hours. ca. 145 mg of finely powdered lysergol as well as a catalytic amount of freshly prepared sodium imidazoletetrahydrofuran solution was added. After 7 days stirring at room temperature the solvent is evaporated to room temperature and the oily residue is chromatographed on Sephadex LH20 with methylene chloride with the addition of 1% methanol to yield the title compound.

The starting material for Example 23 may be made in an analogous manner.

In analogous manner to that described in Example 1 there may be obtained the following compounds of formula I, wherein A is A5; X is dihydrolysergylamino, the 5,6 and 13,14 double bonds are unsaturated, the 15-hydroxy group is (i) α and (ii) β, and:

C is

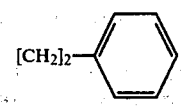

(i)

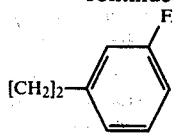 (ii)

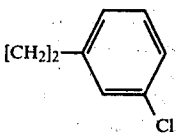 (iii)

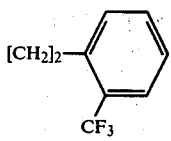 (iv)

CH₂ . CH=CH . [CH₂]₆ . CH₃        (v)

CH₂ . CH=CH₂        (vi)

 (vii)

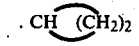 (viii)

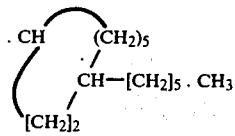 (ix)

The mono-deuterated prostaglandins, especially the compounds of formula I, are useful because they exhibit pharmacological activity in animals, e.g. known prostaglandin-like activity of analogous undeuterated prostaglandins. In particular the prostaglandins especially the PGE, PGF$_\alpha$ and PGA compounds of formula I are useful as broncho-dilator agents, e.g. for the treatment of asthma, and agents for lowering arterial blood pressure (especially the PGA and PGE compounds of formula I) as indicated in standard prostaglandin test for example by their effect on the smooth muscles of the rat stomach and colon on administration of 1 to 100 mg of the compounds in accordance with the principles of N. Gilmore, et al, Nature, 218, 1135–40 (1968) and by their effect on the quinea pig ileum on administration of from 0.3 to 3 µg/ml of the compounds in accordance with the principles of M. Ruegg et al, Exper. 28, 1525 (1972), and R. Jaques, Helv. Physiol. Acta, 17, 255 (1959) and 23, 156 (1965).

For the above use, the dosage will, of course, vary depending on the compound employed, mode of administration and treatment desired. However, satisfactory results are obtained when administered at a daily dosage of from about 0.1 µg to about 100 µg per kg animal body weight, conveniently given in divided doses 2 to 4 times a day or in sustained release form. For the larger mammals, the total daily dosage is in the range from about 0.1 to about 20 mg, and dosage forms suitable for oral administration comprise from about 0.02 mg to about 10 mg of the compounds admixed with a solid or liquid pharmaceutical carrier of diluent.

The prostaglandins, especially the PGE and PGF₂-type compounds, are furthermore useful as uterus-stimulating agents as indicated in standard prostaglandin tests, for example, in the rat uterus in situ on administration of 0.1, e.g. 0.5 to 60 µg/kg animal body weight of the compounds according to the principles of Bisset G. W. et al in Memoirs of the Society for Endocrinology No. 14—Endogenous substances affecting the myometrium (Edited by V. R. Pickles and R. J. Fitzpatrick. Cambridge University Press, 1966, p. 185–188) and in the rat uterus in vitro on administration of from 1 to 100 mg/ml of the compounds in accordance with the principles of P. Holton, Brit. J. Pharmacol., 3, 328 (1949).

For the above use, the dosage will, of course, vary depending on the compound employed, mode of administration and treatment desired. However, in general, satisfactory results are obtained when administered at a daily dosage of from about 0.1 µg to about 100 µg per kg animal body weight, conveniently given in divided doses 2 to 4 times a day or in sustained release form. For the larger mammals, the total daily dosage is in the range from about 0.1 to about 20 mg, and dosage forms suitable for oral administration comprise from about 0.02 mg to about 10 mg of the compounds admixed with a solid or liquid pharmaceutical carrier or diluent.

Furthermore, the prostaglandins are useful as nasal decongestant agents as indicated in standard prostaglandin tests for indicating nasal decongestion in animals. They can be administered in amounts from about 10 µg/ml to about 0.1 mg/ml with a liquid pharmaceutical diluent.

For the above use, the dosage will, of course, vary depending on the compound employed, mode of administration and treatment desired. However, in general, satisfactory results are obtained when administered at a daily dosage of from about 0.1 µg to about 100 µg per kg animal body weight, conveniently given in divided doses 2 to 4 times a day or in sustained release form. For the larger mammals, the total daily dosage is in the range from about 0.1 to about 20 mg, and dosage forms suitable for oral administration comprise from about 0.02 mg to about 10 mg of the compounds admixed with a solid or liquid pharmaceutical carrier or diluent.

When the compounds are administered in liquid form, for example as nasal decongestant agents, they are conveniently administered in a form of a liquid pharmaceutical composition containing about 10 µg to about 20 µg per ml of liquid.

Furthermore, the prostaglandins, and especially the PGE and PGF$_{2\alpha}$ compounds of formula I, are useful as inhibitors of blood platelet aggregation as indicated in standard prostaglandin tests for indicating blood platelet aggregation.

For the above use, the dosage will, of course, vary depending on the compound employed, mod of administration and treatment desired. However, in general, satisfactory results are obtained when administered at a daily dosage of from about 0.1 µg to about 100 µg per kg animal body weight, conveniently given in divided doses 2 to 4 times a day or in sustained release form. For the larger mammals, the total daily dosage is in the range from about 0.1 to about 20 mg, and dosage forms suitable for oral administration comprise from about 0.02 mg to about 10 mg of the compounds admixed with a solid or liquid pharmaceutical carrier or diluent.

The PGE and PGF₂ prostaglandins are furthermore useful as gastric secretion inhibitors as indicated in standard tests, for example, in rats on administration of from 1 to 100 µg/kg animal body weight of the compounds by an inhibition of penta-gastrin and histamine induced gastric secretion according to the principles of M. N.

Gosh et al., Brit. J. Pharmacol., 13, 54 (1958) and F. Halter et al in Helv. med. Acta, suppl., 50, 113 (1971).

For the above use, the dosage will, of course, vary depending on the compound employed, mode of administration and treatment desired. However, in general, satisfactory results are obtained when administered at a daily dosage of from about 0.1 µg to about 100 µg per kg animal body weight, conveniently given in divided doses 2 to 4 times a day or in sustained release form. For the larger mammals, the total daily dosage is in the range from about 0.1 to about 20 mg, and dosage forms suitable for oral administration comprise from about 0.02 mg to about 10 mg of the compounds admixed with a solid or liquid pharmaceutical carrier of diluent.

The prostaglandins may be administered in pharmaceutically acceptable salt form. Such salt forms exhibit the same order of activity as the free acid forms. Representative salt forms include alkali metal salts such as the sodium or potassium salt, alkaline earth metal salts such as the calcium salt and also include organic salts such as the ammonium salt and amine salts such as the dimethylamine, diethylamine, trimethylamine and benzylamine salts.

The prostaglandins may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional tecniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents, such as starch, gelatin and acacia, the lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastro-intestinal tract and thereby provide sustained action over a long period.

The preferred compositions from the standpoint of ease of administration are solid compositions, particularly solid-filled gelatin capsules and tablets.

We claim:

1. A compound which is 15-deutero-11α,15R-dihydroxy-16,16-dimethyl-9-keto-2,3-(+)-trans-methylene-prosta-5cis,13 trans-dienoic acid.

2. A compound which is 15-deutero-11α,15R-dihydroxy-16,16-dimethyl-9-keto-2,3-(−)-trans-methylene-prosta-5cis,13 trans-dienoic acid.

3. A compound which is 15-deutero-16,16-dimethyl-2,3-(−)trans-methylene-9α,11α,15R-trihydroxy-prosta-5cis,13 trans-dienoic acid.

* * * * *

UNITED STATES PATENT AND TRADEMARK OFFICE
CERTIFICATE OF CORRECTION

PATENT NO. : 4,259,523

DATED : March 31, 1981

INVENTOR(S) : PIETRO BOLLINGER et al.

It is certified that error appears in the above-identified patent and that said Letters Patent is hereby corrected as shown below:

Title page, left-hand column; directly beneath the bold heading "United States Patent" at the top of the column, change "Bollingen et al." to --Bollinger et al.--

Title page, left-hand column; directly beneath the title "ORGANIC COMPOUNDS" and to the right of "Inventors:", change the spelling of the last name of the first-named inventor to read --Bollinger--.

Title page, left-hand column; directly beneath the last line of the cross-reference under the heading "Related U.S. Application Data", please insert the heading entitled --Foreign Application Priority Data-- and directly beneath the new heading, insert --June 25, 1975[CH] Switzerland 8250/75--.

Column 1, in the row of structural formulae beneath line 38; delete the formula

" 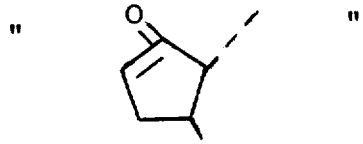 "

UNITED STATES PATENT AND TRADEMARK OFFICE
CERTIFICATE OF CORRECTION

PATENT NO. : 4,259,523

DATED : March 11, 1981

INVENTOR(S) : PIETRO BOLLINGER et al.

It is certified that error appears in the above-identified patent and that said Letters Patent is hereby corrected as shown below:

and substitute therefor

-- 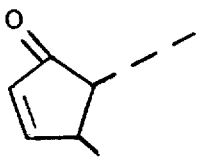 --

Signed and Sealed this

Fourth Day of January 1983

[SEAL]

Attest:

Attesting Officer

GERALD J. MOSSINGHOFF

Commissioner of Patents and Trademarks